Aug. 9, 1960 W. C. McDONALD Plant Pat. 1,965
ROSE PLANT
Filed Oct. 26, 1959
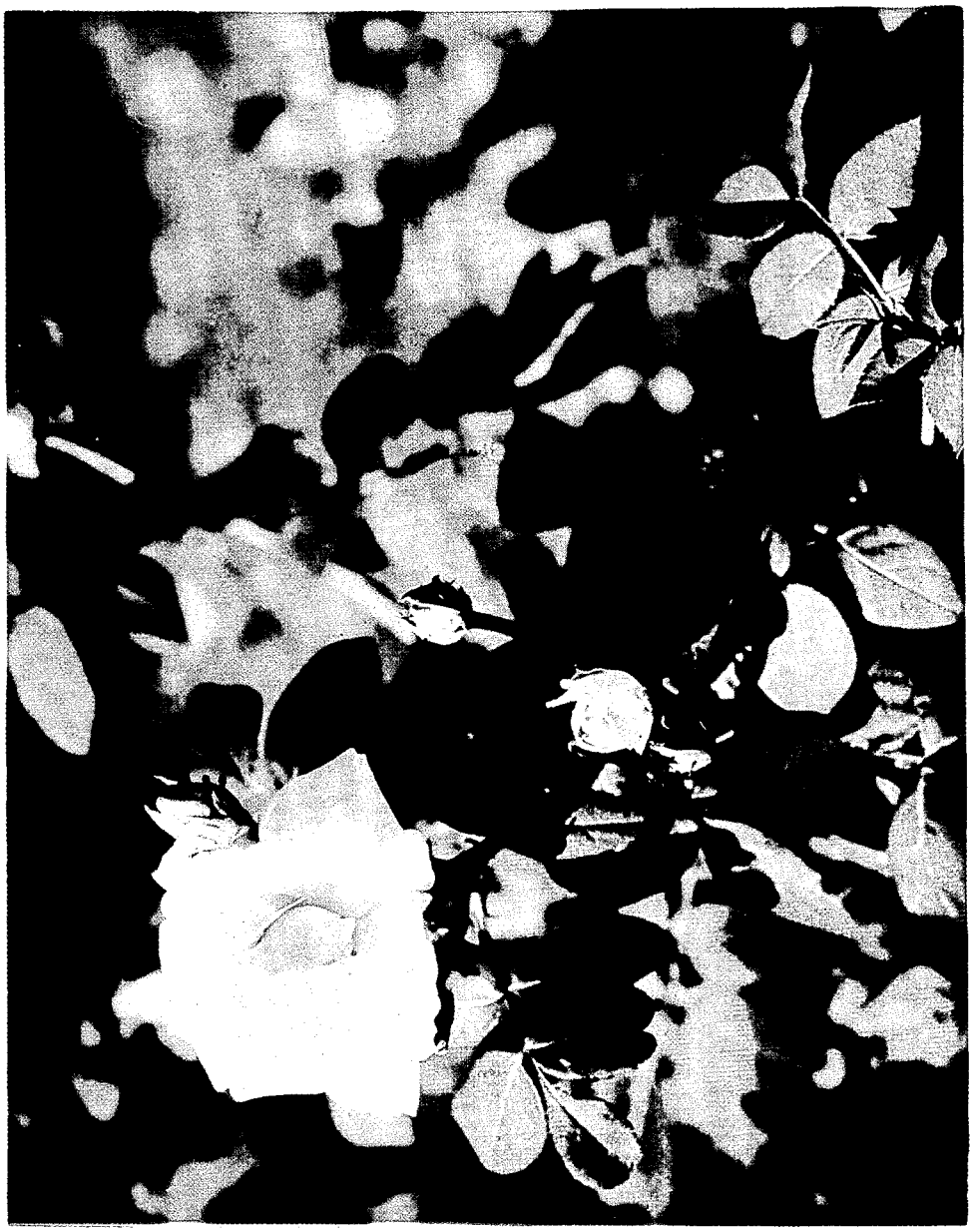
INVENTOR
William C. McDonald
BY Robb & Robb
ATTORNEYS United States Patent Office Plant Pat. 1,965
Patented Aug. 9, 1960

1,965

ROSE PLANT

William C. McDonald, 914 N. Adams St., San Angelo, Tex.

Filed Oct. 26, 1959, Ser. No. 848,881

1 Claim. (Cl. 47—61)

The present invention relates to a new and distinct variety of rose plant of the large-flowered polyantha class, which originated as a sport of the variety known as "Ma Perkins" (Plant Patent No. 1,143).

This new variety was initially discovered by me amongst plantings of the variety "Ma Perkins" in my garden on my own property at San Angelo, Texas. During cultivation of these plants, my attention was attracted to a particular plant on which the flowers exhibited a distinctive white color which was appreciably different from the normal coloration of the flowers of the variety "Ma Perkins," which ordinarily bears flowers ranging in color to coral, salmon or pink, according to geographical location, soil and/or climate variations. Upon closer examination of the particular plant to which my attention was attracted, I found that it had sported, and I thereupon took steps to preserve the sport, keep it under observation, and later to asexually reproduce the same.

Continued observations of the original plant and the asexual reproductions thereof as performed by me by budding, at San Angelo, Texas, fully confirmed that the unique snow white color of the flowers was definitely fixed and established, and that these characteristics are transmissible through succeeding propagations.

These observations additionally established that the new sport otherwise generally corresponded to the characteristics of the parent variety "Ma Perkins," except that the foliage color was a slightly lighter shade of green; the plants bloomed more profusely than the parent variety; as a whole, could better withstand hot weather; and the flowers were somewhat more fragrant. Accordingly, the new sport is dominantly characterized by the following unique combination of features which differentiate it from the parent variety, as well as from all other varieties of which I am aware:

(1) General similarities to the variety "Ma Perkins," but with a lighter green foliage color;
(2) A more profuse blooming habit;
(3) Greater tolerance to hot weather;
(4) A distinctive snow white flower color; and
(5) A stronger flower fragrance.

The accompanying drawing shows a typical specimen plant of my new variety, with the foliage and flowers in different stages of development and depicted in color as nearly true as it is reasonably possible to make the same in a color illustration of this character.

In view of the similarities in general characteristics between the new variety and its parent "Ma Perkins," excepting for the aforementioned distinctions, it is unnecessary to further describe the new variety in detail, since these details largely conform to those appearing in Plant Patent No. 1,143, dated November 4, 1952, to which reference may be readily had.

I claim:

A new and distinct variety of rose plant of the large-flowered polyantha class, substantially as herein shown and described, characterized particularly as to novelty by the unique combination of general similarities to the characteristics of the parent variety "Ma Perkins" (Plant Patent No. 1,143), but from which it is essentially distinguished by a slightly lighter green color of the foliage, a more profuse blooming habit, greater tolerance to hot weather, a distinctive snow white flower color, and a stronger fragrance of the flowers.

No references cited.